(12) United States Patent
Tatsumi

(10) Patent No.: US 7,597,851 B2
(45) Date of Patent: Oct. 6, 2009

(54) AUTOMATIC SAMPLER AND METHOD FOR RINSING NEEDLE OF THE SAME

(75) Inventor: Nobuyuki Tatsumi, Kyoto (JP)

(73) Assignee: Shimadzu Corporation, Kyoto-shi (JP)

( * ) Notice: Subject to any disclaimer, the term of this patent is extended or adjusted under 35 U.S.C. 154(b) by 806 days.

(21) Appl. No.: 10/779,943

(22) Filed: Feb. 17, 2004

(65) Prior Publication Data

US 2004/0175833 A1    Sep. 9, 2004

(30) Foreign Application Priority Data

Mar. 5, 2003   (JP) .............................. 2003-059062

(51) Int. Cl.
  *B01L 3/02* (2006.01)
(52) U.S. Cl. .................................... 422/100
(58) Field of Classification Search ................ 210/198, 210/198.2, 656; 73/61.55; 436/61; 422/100, 422/99, 104, 102
See application file for complete search history.

(56) References Cited

FOREIGN PATENT DOCUMENTS

| JP | 8-10797 | 3/1996 |
| JP | 09-127078 | 5/1997 |
| JP | 3142606 | * 12/2000 |

OTHER PUBLICATIONS

PTO 07/5633, English Translation of JP3142606B2. Goto e tal, Jul. 2007.*
Product Literature of AOC-20 Series Automatic Sampling System. Date: Dec. 12, 2000.*
Product Literature of AOC-17 Auto Injector. Date: Dec. 12, 2000.*

* cited by examiner

*Primary Examiner*—Walter D Griffin
*Assistant Examiner*—Bobby Ramdhanie
(74) *Attorney, Agent, or Firm*—Rankin, Hill & Clark LLP

(57) ABSTRACT

An automatic sampler comprises a first rinsing bath for rinsing the needle by soaking the needle in a rinsing liquid, in which the rinsing liquid is reserved, and a second rinsing bath for rinsing the needle by soaking the needle in a rinsing liquid, in which the rinsing liquid is exchanged during the rinsing operation. The first rinsing bath and the second rinsing bath are selectively employed for the purpose of use. That is, when a high rinsing power is required, such as when cross contamination is prevented, the second rinsing bath having higher rinsing power is employed. On the other hand, when the throughput is emphasized, the first rinsing bath is employed to rinse the needle in a shorter time.

5 Claims, 3 Drawing Sheets

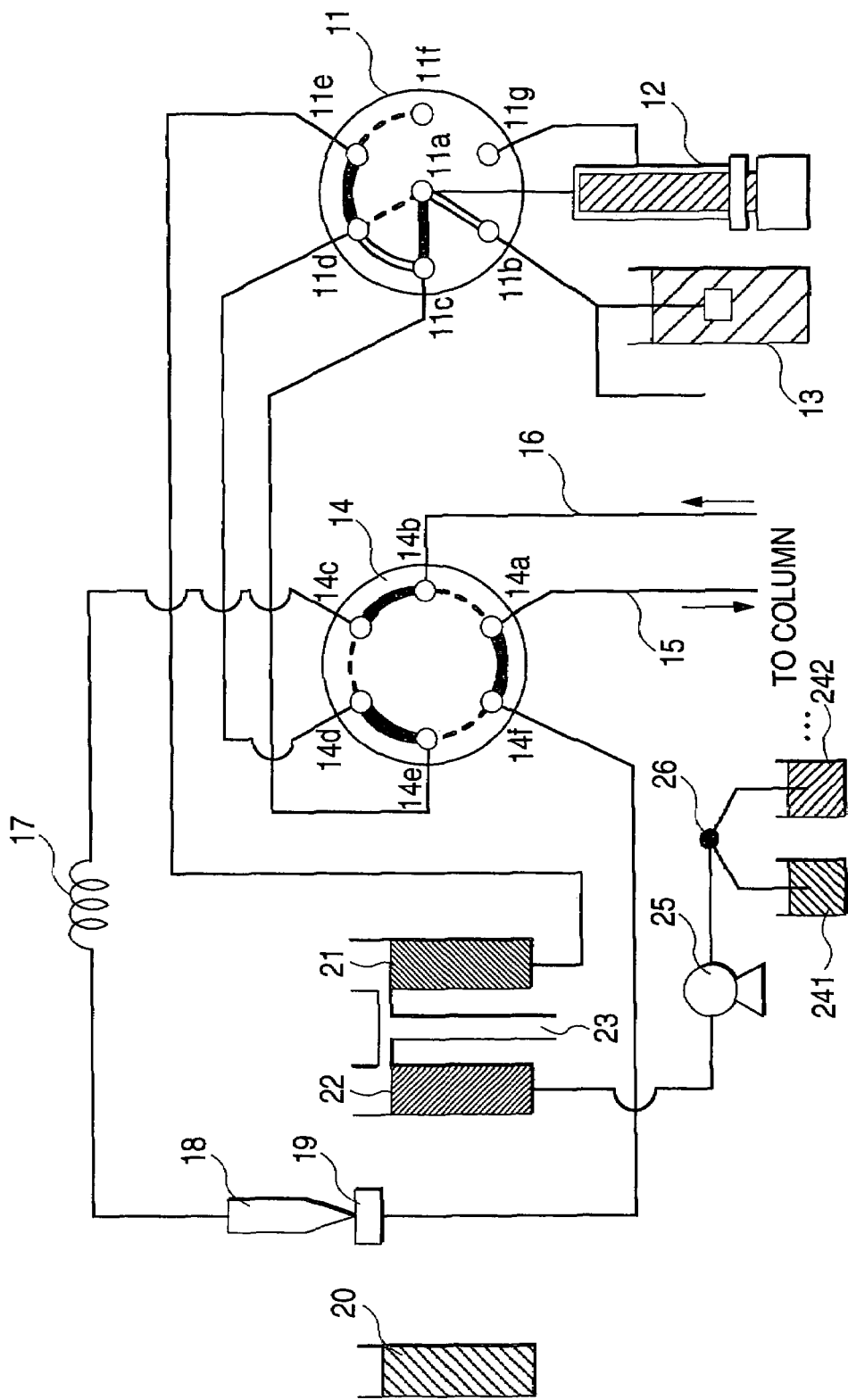

AUTOMATIC SAMPLER AND METHOD FOR RINSING NEEDLE OF THE SAME

BACKGROUND OF THE INVENTION

1. Field of the Invention

The present invention relates to an automatic sample injecting device (automatic sampler) for use to introduce a sample into a liquid chromatography, and a method for rinsing a needle of an automatic sampler.

2. Description of the Related Art

In the liquid chromatography (LC), the automatic sampler is used to introduce a predetermined amount of sample into a column. A sample injecting operation using the automatic sampler involves, first of all, inserting a needle into a vessel in which the sample is placed, and sucking and holding the predetermined amount of sample via the needle into a sample loop or the like. Then, the needle is moved to an injection port communicating to the column of the LC, and the held sample is injected into the injection port.

In performing an injecting operation of certain sample, if a residue of the sample used at the previous measurement adheres to the needle, a measurement error is caused by cross contamination. Therefore, the needle is rinsed before performing the injecting operation of sample. This rinsing operation is usually made by reserving a rinsing liquid in a rinsing bath and soaking the needle in the rinsing liquid as described as the related art in JP-A-9-127078 ([0004] and [0005], FIG. 2).

With this method, there is an advantage that the rinsing operation is finished in a short time, because it is only necessary that the needle is soaked in the rinsing liquid. On the contrary, there is the possibility that a sample liquid diluted by the rinsing liquid may adhere to the needle and be left on the needle, resulting in a risk that this residue may cause an error at the next measurement.

In this automatic sampler, there are various uses for the purpose of measurement where the throughput is emphasized or the measurement at high precision is desired by enhancing the rinsing performance at the expense of the throughput to some extent. In the related-art devices, such requirements were not satisfied.

SUMMARY OF THE INVENTION

It is an object of the invention to provide an automatic sampler capable of rinsing the needle by a suitable method for the purpose of measurement, and a method for rinsing a needle of an automatic sampler.

In order to achieve the above object, the present invention provides an automatic sampler for injecting a sample into a sample introducing portion in communication to a column of a liquid chromatography, comprising:

a) a needle for sucking the sample from a sample liquid bath and injecting the sample into the sample introducing portion;

b) a first rinsing section for rinsing the needle by soaking the needle in a first rinsing liquid, in which the first rinsing liquid is not exchanged during the rinsing operation; and c) a second rinsing section for rinsing the needle by soaking the needle in a second rinsing liquid, in which the second rinsing liquid is exchanged during the rinsing operation, wherein the needle is rinsed by at least one rinsing section selected from the first rinsing section and the second rinsing section.

BRIEF DESCRIPTION OF THE DRAWINGS

FIG. 3 is a schematic constitutional view showing another embodiment of an automatic sampler provided with a switching valve of a second rinsing liquid.

DETAILED DESCRIPTION OF THE INVENTION

Figure 1:
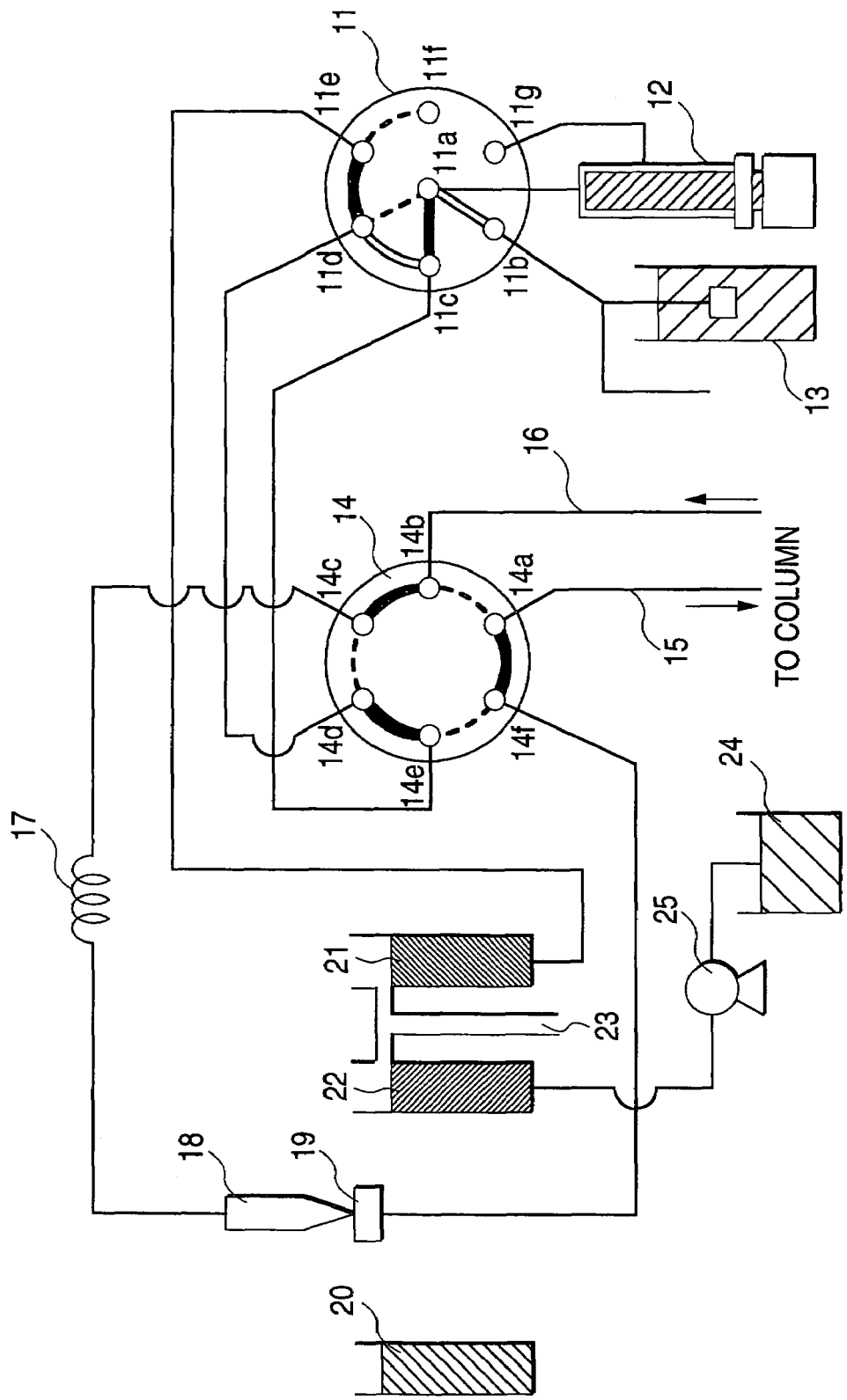
FIG. 1 is a schematic constitutional view showing one embodiment of an automatic sampler according to the present invention.

In an automatic sampler of the present invention, two independent rinsing sections are provided. A first rinsing section rinses a needle by soaking it in a rinsing liquid (first rinsing liquid) that is reserved in a rinsing bath (first rinsing bath). The rinsing liquid in the first rinsing bath is not exchanged during this rinsing operation. The rinsing liquid may be exchanged by injecting the new rinsing liquid into the first rinsing bath at a certain time when the rinsing operation is not performed. On the other hand, a second rinsing section rinses the needle by inserting the needle into a rinsing bath (second rinsing bath) and then supplying the rinsing liquid (second rinsing liquid) into the second rinsing bath. By supply of this rinsing liquid, the old rinsing liquid within the second rinsing bath is exhausted through an exhaust opening of the second rinsing bath. Accordingly, the second rinsing liquid is exchanged in the second rinsing bath during the rinsing operation.

In the first rinsing section, the first rinsing liquid is reserved in advance in the first rinsing bath before the rinsing operation, and the needle is soaked in the first rinsing bath for a predetermined rinsing time, whereby the rinsing time is shorter than the second rinsing section. Further, the amount of rinsing liquid consumed for one time of rinsing operation is less than the second rinsing section.

On the other hand, in the second rinsing section, the rinsing liquid contaminated by the sample during the rinsing operation is rapidly exhausted through the exhaust opening of the second rinsing bath, and the new rinsing liquid is supplied. Therefore, the residual sample in the rinsing liquid is prevented from adhering to the needle again, whereby the rinsing performance is higher than the first rinsing section.

In this way, the first rinsing section and the second rinsing section have advantages complementary to each other. To utilize these advantages, the first rinsing section and the second rinsing section are selectively used according to the purpose of use. That is, the first rinsing section may be used in the case where an error by cross contamination is less significant, or the throughput is higher in priority than the error. On the other hand, the second rinsing section may be used in the case where the cross contamination has sensitive influence to give priority to the rinsing performance.

Since the feature of each rinsing section exists in the rinsing operation (presence or absence of exchanging the rinsing liquid), as previously described, the first rinsing liquid and the second rinsing liquid may be of the same kind when these features are simply considered. Moreover, if the first rinsing liquid and the second rinsing liquid are of different kinds, the rinsing operation may be performed more appropriately by combining the rinsing operation with the kind of rinsing liquid.

In addition, both the rinsing sections may be combined during one time of rinsing operation. That is, the rinsing operation is performed in one rinsing bath, and subsequently in another rinsing bath. For example, when a residual sample containing a plurality of constituents adheres to the needle, first of all, some of the constituents are removed in the first rinsing bath, and the remaining constituents on the needle are removed in the second rinsing bath.

Moreover, the automatic sampler of the invention may comprise a switching section for selecting the second rinsing liquid for use in the second rinsing section from a plurality of rinsing liquids. In the rinsing operation with the second rinsing section, the second rinsing liquid is changed, when two or more kinds of rinsing liquid are selectively used depending on the kind of sample adhering to the needle. This switching section may be a three-way valve.

EFFECT OF THE INVENTION

With this invention, two kinds of rinsing sections are selectively used, whereby the needle is rinsed by a more appropriate rinsing method, according to the purpose of measurement. That is, when the throughput is given priority, the first rinsing section is employed to rinse the needle in a short time. On the other hand, when a smaller error by cross contamination is given priority, the second rinsing section is employed to rinse the needle with higher power. Further, the kind of rinsing liquid used by the second rinsing section is switched, thereby rinsing the needle in a rinsing liquid according to the kind of sample adhering to the needle.

EMBODIMENTS (1) Constitution of one Embodiment of Automatic Sampler According to the Invention One embodiment of automatic sampler according to the invention will be described below. FIG. 1 is a schematic constitutional view showing the embodiment of automatic sampler. A first valve 11 consisting of a 7-port 6-position valve has seven ports 11a to 11g. The port 11a is connected with a metering syringe 12. The port 11b is connected with a first rinsing liquid tank 13 and the port 11e is connected with a first rinsing bath 21. A second valve consisting of a six-way valve has six ports 14a to 14f for selectively connecting adjacent ports by a switching operation. The port 14a is connected with a liquid feed pipe 15 for feeding a liquid of sample to a column of a liquid chromatography, and the port 14b is connected with a liquid feed pipe 16 for supplying a mobile phase to the column. The ports 14d and 14e are connected with the port 11d and the port 11c of the first valve 11, respectively. The port 14c is connected with one end of a sample loop 17, the other end of this sample loop 17 being connected to a needle 18. The port 14f is connected with an injection port 19. The needle 18 has a movable mechanism for moving from the injection port 19 to a sample vessel 20, the first rinsing bath 21, and a second rinsing bath 22, and entering into the liquid of vessel or each bath.

The first rinsing bath 21 reserves a first rinsing liquid by injecting the first rinsing liquid in the first rinsing liquid tank 13 via the metering syringe 12, the port 11a, and the port 11e. The injecting operation of the first rinsing liquid will be described later. The second rinsing bath 22 is connected with a pump 25 for injecting a second rinsing liquid from a second rinsing liquid tank 24 to the second rinsing bath 22.

(2) Sample Injecting Operation of this Embodiment

First of all, an injecting operation of sample into the automatic sampler of this embodiment will be described before the rinsing operation of the needle that is a feature of this invention will be described. Firstly, the second valve 14 is switched to a connected state as indicated by the solid line in FIG. 1. The needle 18 is placed at a position on the injection port 19. A mobile phase is fed from the liquid feed pipe 16 through the sample loop 17, the needle 18, and the injection port 19 to the liquid feed pipe 15, and filled in this flow passage.

Then, the second valve 14 is switched to a connected state as indicated by the broken line in FIG. 1, and the first valve 11 is switched to a connected state as indicated by the broken line in FIG. 1. Thereby, the metering syringe 12 and the needle 18 are connected via the ports 11a, 11d, 14d and 14c through the sample loop 17. The needle 18 is moved onto the sample vessel 20, and inserted into the sample vessel 20. Owing to a suction operation of the metering syringe 12, a predetermined amount of sample is sucked and held from the sample vessel 20 into the sample loop 17.

After the completion of sucking the sample, the needle 18 is restored to a position on the injection port 19. The second valve 12 is restored to the connected state as indicated by the solid line in FIG. 1. Thereby, a mobile phase is fed from the liquid feed pipe 16 through the sample loop 17, the needle 18, and the injection port 19 into the liquid feed pipe 15. In this way, the sample held through the sample loop 17 is supplied to the column of the liquid chromatography, together with the mobile phase.

Herein, since some sample adheres to the outside the needle 18, the needle 18 is rinsed at an appropriate time before starting the next injecting operation of sample, as will be described later.

(3) Needle Rinsing Operation of this Embodiment

The rinsing operation of needle that is a feature of this invention will be described below. Before starting the measurement, the measurer sets up the following items for the rinsing conditions of needle by making a predetermined operation. First of all, the "rinsing timing" of needle is selected from (i) Before the sample injecting operation, (ii) After the sample injecting operation, (iii) Before and after the sample injecting operation, and (iv) No rinse When the "rinsing timing" is selected from (i) to (iii), the "rinsing bath to be used" is selected from (i) Using only the first rinsing bath, (ii) Using only the second rinsing bath, (iii) Using the first rinsing bath and the second rinsing bath consecutively, and (iv) Using the second rinsing bath only when the kind of sample is changed and using the first rinsing bath in other time.

When the "rinsing timing" is selected at (iii), selection of the "rinsing bath to be used" may be made for each of before and after the sample injecting operation. Then, the rinsing time is set up. This rinsing time is set up by the time for soaking the needle 18 in the rinsing liquid.

Figure 2A:
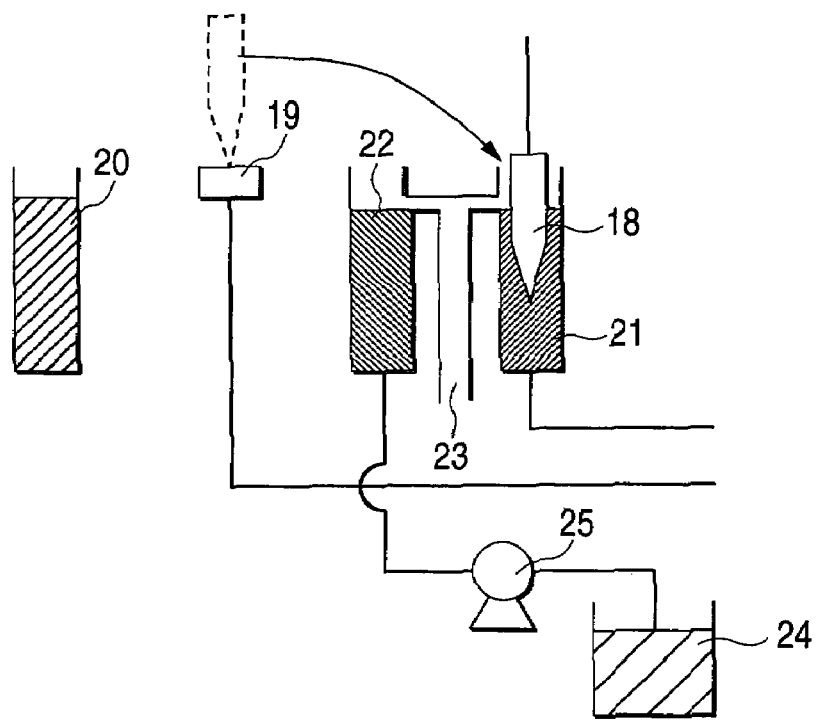
FIGS. 2A and 2B are views for explaining a rinsing operation of a needle in the embodiment shown in FIG. 1.

The needle is rinsed in the following way in accordance with the set up rinsing conditions of the needle. When the rinsing operation is made in the first rinsing bath, first of all, the first valve 11 is switched to a connected state as indicated by the double line. The metering syringe 12 sucks a predetermined amount of first rinsing liquid from the first rinsing liquid tank 13. Then, the first valve 11 is switched to a connected state as indicated by the solid line in FIG. 1. The first rinsing liquid in the metering syringe 12 is supplied via the ports 11a, 11c, 14e, 14d, 11d and 11e to the first rinsing bath 21. The used rinsing liquid remaining in the first rinsing bath and excessively injected rinsing liquid are exhausted from an exhaust opening 23. Thereafter, the needle 18 is inserted into the first rinsing bath 21, and soaked in the first rinsing liquid for a set up time (FIG. 2A). Thereby, the needle 18 is rinsed. During the rinsing operation, supply of the first rinsing liquid into the first rinsing bath 21, namely, exchange of the first rinsing liquid, is not performed. After the predetermined time has passed, the needle 18 is moved to a predetermined position, whereby the rinsing operation is ended. Herein, when the "rinsing bath to be used" is selected to be (i) or (ii), the predetermined position is the injection port 19 or the sample vessel 20. On the other hand, when the "rinsing bath to be used" is selected to be (iii), the predetermined position is the second rinsing bath 22, whereby the second rinsing bath is successively employed for rinsing.

Figure 2B:
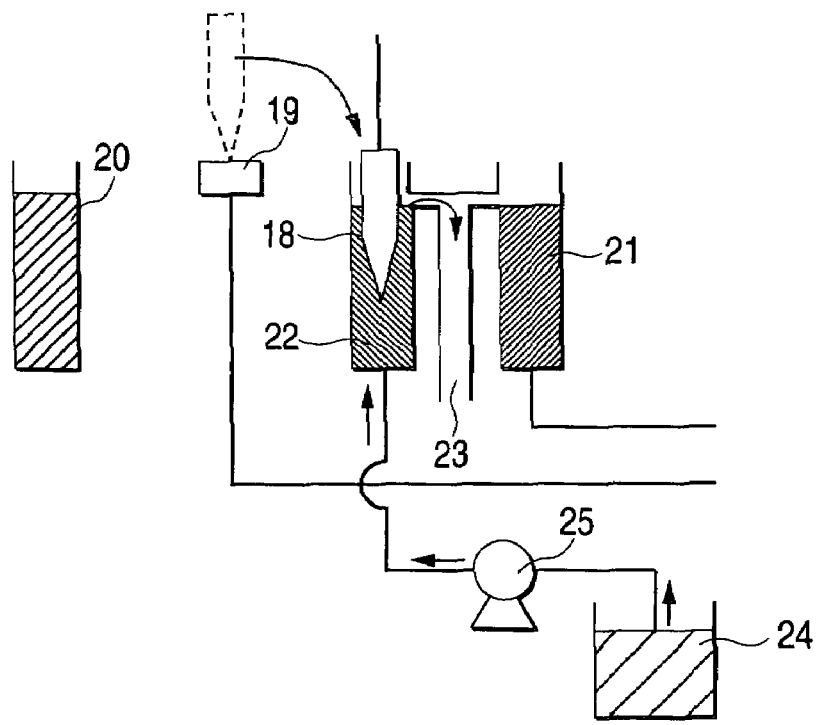

When the second rinsing bath is employed for rinsing, the needle 18 is inserted into the second rinsing bath 22, and the pump 25 is activated to flow the second rinsing liquid into the second rinsing bath 22. The needle 18 is rinsed by soaking the needle 18 into the second rinsing liquid for the set up rinsing time (FIG. 2B). Meanwhile, the second rinsing liquid is flowed into the second rinsing bath 22 and exhausted from the exhaust opening 23. Therefore, the sample adhering to the needle 18 is exhausted from the exhaust opening 23, together with the second rinsing liquid. In this way, the residual sample in the rinsing liquid is prevented from adhering to the needle 18 again, so that the needle 18 is rinsed within the second rinsing bath at high performance. After the elapse of the rinsing time, the needle 18 is moved to the predetermined position, whereby the rising operation is ended.

(4) Example of Selectively Using the Rinsing Bath

The first rinsing bath is effective for simple rinsing operation, while the second rinsing bath is effective when requiring a high rinsing power, as previously described. Therefore, it is desirable that both the rinsing baths are selectively employed by utilizing the advantages of rinsing baths. The following (a) to (c) show the examples of selectively employing the rinsing baths, and the "rinsing bath to be used" and the "rinsing timing" as setting items for the rinsing conditions of the needle are given desired settings.

(a) When the Throughput is Given Higher Priority than the Rinsing Performance

In this case, the "rinsing bath to be used" (i) is selected so that the rinsing time may be shorter. The "rinsing timing" may be any of (i) to (iii).

(b) When the Sample is Denatured with the Rinsing Liquid

For instance, in rinsing the needle having adhering constituents such as protein, those constituents may be denatured with the rinsing liquid, and adhere to the needle. In this case, the "rinsing bath to be used" (iii) is effectively selected. Herein, the first rinsing liquid should not denature the sample (but may have relatively low rinsing effect), and the second rinsing liquid should have the high rinsing effect (but may denature the sample). That is, after the denaturable constituents are removed from the needle in the first rinsing bath, and other constituents are fully removed in the second rinsing bath. Thereby, it is possible to prevent the denatured sample from fixing and other constituents from remaining. The "rinsing timing" may be any of (i) to (iii).

(c) When Mixture of Different Kinds of Samples is Prevented

When the measurement is made by changing the kind of sample to be measured, the "rinsing bath to be used" (iv) is selected. This is made by rinsing the needle at high throughout, employing the first rinsing bath, while the same kind of sample is being measured, and rinsing the needle with higher performance, employing the second rinsing bath, only when different kind of sample is measured. Thereby, the rinsing operation with enhanced throughput is simply performed while preventing different kind of sample from being mixed.

(5) Modified Embodiment

In this embodiment, a switching valve of the second rinsing liquid is provided to enable more two kinds of second rinsing liquids to be selectively employed. This modified embodiment is shown in FIG. 3. This embodiment is different from the device of FIG. 1 in that a plurality of second rinsing liquid tanks 241, 242, . . . are provided to allow a plurality of second rinsing liquids to be supplied to the second rinsing bath, and a second rinsing liquid switching valve 26 is provided to connect the second rinsing liquid tanks and the pump 25. The second rinsing liquid to be supplied to the second rinsing bath is switched by this second rinsing liquid switching valve 26.

Thereby, when the rinsing operation is made in the second rinsing bath, the second rinsing liquid is switched for each used sample, so that the optimal second rinsing liquid may be employed, thereby further enhancing the rinsing power. For instance, a basic rinsing liquid is employed for acid sample, and an acid rinsing liquid is employed for basic sample. Also, an aqueous rinsing liquid is employed for water-soluble sample, and an organic solvent is employed for oil soluble sample.

Also, when the constitution of this modified embodiment is employed, the measurer selects the "rinsing bath to be used" from (i) to (iv) in setting up the rinsing conditions of the needle, and further selects the second rinsing liquid for each measured sample.

What is claimed is:

1. An automatic sampler, comprising:
   a needle adapted to draw a sample from a sample liquid bath and to inject the sample into a sample introducing portion which is in fluid communication with a column of a liquid chromatography;
   a first rinsing bath adapted to contain a first rinsing liquid;
   a second rinsing bath adapted to contain at least one kind of second rinsing liquid;
   an exchanging mechanism operable to exchange the second rinsing liquid in the second rinsing bath; and
   a controller, configured to execute, in accordance with selection of an operator, at least one of a first rinsing operation which soaks the needle in the first rinsing liquid in the first rinsing bath, and a second rinsing operation which soaks the needle in the second rinsing liquid in the second rinsing bath and exchanges the second rinsing liquid while the needle is kept inserted into the second rinsing bath.

2. A method for rinsing a needle of an automatic sampler, said method comprising:
   providing a first rinsing bath containing a first rinsing liquid;
   providing a second rinsing bath substantially filled with a second rinsing liquid;
   causing an operator to select at least one of a first rinsing operation in which the needle is soaked in the first rinsing liquid in the first rinsing bath, and a second rinsing operation in which the needle is soaked in the second rinsing liquid in the second rinsing bath and the second rinsing liquid is exchanged while the needle is kept inserted into the second rinsing bath, the second rinsing liquid being exchanged by overflowing from a top opening of the second rinsing bath when the needle is soaked therein while simultaneously introducing second rinsing liquid into the second rinsing bath; and executing the at least one of the first rinsing operation and the second rinsing operation selected by the operator.

3. The method for rinsing a needle of an automatic sampler according to claim 2, further comprising:

selecting one of plural kinds of liquid as the second rinsing liquid to be supplied to the second rinsing bath to exchange the second rinsing liquid in the second rinsing bath.

4. An automatic sampler, comprising:

a needle adapted to draw a sample from a sample liquid bath and to inject the sample into a sample introducing portion which is in fluid communication with a column of a liquid chromatography;

a first rinsing bath adapted to contain first rinsing liquid;

a second rinsing bath having a top opening and adapted to contain at least one kind of second rinsing liquid;

a controller, configured to execute at least one of a first rinsing operation which soaks the needle in the first rinsing liquid in the first rinsing bath, and a second rinsing operation which soaks the needle in the second rinsing liquid in the second rinsing bath and exchanges the second rinsing liquid while the needle is kept inserted into the second rinsing bath;

a pump fluidly connected to the second liquid bath irrespective of a position of the needle; and an exhaust adjacent to the top opening of the second rinsing bath, wherein said pump is configured to be controlled by the controller to supply the second rinsing liquid to the second rinsing bath such that the second rinsing liquid in the second rinsing bath overflows into the exhaust when the needle is soaked in the second rinsing bath so as to exchange the second rinsing liquid in the second rinsing bath.

5. The automatic sampler according to claim 4, further comprising:

a switcher, configured to select one of plural kinds of liquid as the second rinsing liquid supplied to the second rinsing bath.

* * * * *